United States Patent
Pedersen

(10) Patent No.: US 9,901,685 B2
(45) Date of Patent: Feb. 27, 2018

(54) INJECTION DEVICE WITH A SLIDING SCALE

(71) Applicant: Novo Nordisk A/S, Bagsvaerd (DK)

(72) Inventor: Simon M. Pedersen, Copenhagen N (DK)

(73) Assignee: Novo Nordisk A/S, Bagsvaerd (DK)

(*) Notice: Subject to any disclaimer, the term of this patent is extended or adjusted under 35 U.S.C. 154(b) by 802 days.

(21) Appl. No.: 14/374,302

(22) PCT Filed: Jan. 17, 2013

(86) PCT No.: PCT/EP2013/050806
§ 371 (c)(1),
(2) Date: Jul. 24, 2014

(87) PCT Pub. No.: WO2013/110538
PCT Pub. Date: Aug. 1, 2013

(65) Prior Publication Data
US 2015/0038915 A1    Feb. 5, 2015

Related U.S. Application Data

(60) Provisional application No. 61/593,956, filed on Feb. 2, 2012.

(30) Foreign Application Priority Data

Jan. 27, 2012  (EP) ..................... 12152847

(51) Int. Cl.
*A61M 5/315* (2006.01)
*A61M 5/20* (2006.01)
*A61M 5/31* (2006.01)

(52) U.S. Cl.
CPC ...... *A61M 5/31553* (2013.01); *A61M 5/2033* (2013.01); *A61M 2005/3126* (2013.01)

(58) Field of Classification Search
CPC ............ A61M 5/2033; A61M 5/31525; A61M 5/31528; A61M 5/31533; A61M 5/3155;
(Continued)

(56) References Cited

U.S. PATENT DOCUMENTS 5,921,966 A    7/1999  Bendek et al.
5,961,495 A   10/1999  Walters et al.
(Continued)

FOREIGN PATENT DOCUMENTS

CN    101084028 A    12/2007
CN    102292120 A    12/2011
(Continued)

OTHER PUBLICATIONS

Summons and Preliminary Opinion from the Opposition Division in EP 2806925, Jan. 6, 2017.
(Continued)

*Primary Examiner* — Kami A Bosworth
(74) *Attorney, Agent, or Firm* — Wesley Nicolas

(57) ABSTRACT

The present invention relates to an injection device for automatic spring driven injection of a liquid drug. The injection device has a dose setting mechanism by which doses of an individual size can be set by a user, and a mechanical dose size display for displaying the size of the set dose. The scale drum (20) is coupled to a rotatable dose dial button (10) which is axially retained in relation to the housing (2) and by which the individual doses can be set.

8 Claims, 4 Drawing Sheets

(58) Field of Classification Search
CPC .......... A61M 5/31551; A61M 5/31553; A61M 5/31556; A61M 5/31558; A61M 5/3156; A61M 5/31561; A61M 5/31563; A61M 5/3159; A61M 5/31591; A61M 5/31593; A61M 2005/2026; A61M 2005/3125; A61M 2005/3126
See application file for complete search history.

(56) References Cited

U.S. PATENT DOCUMENTS

| | | | |
|---|---|---|---|
| 6,004,297 | A | 12/1999 | Steenfeldt-Jensen et al. |
| 6,228,067 | B1 | 5/2001 | Gabriel |
| 6,899,699 | B2 | 5/2005 | Enggaard |
| 7,427,275 | B2 | 9/2008 | DeRuntz et al. |
| 8,357,120 | B2 | 1/2013 | Moller et al. |
| 2006/0258988 | A1 | 11/2006 | Keitel et al. |
| 2007/0129687 | A1 | 6/2007 | Marshall et al. |
| 2008/0269688 | A1 | 10/2008 | Colucci et al. |
| 2008/0306445 | A1 | 12/2008 | Burren et al. |
| 2008/0306446 | A1 | 12/2008 | Markussen |
| 2009/0048561 | A1 | 2/2009 | Burren et al. |
| 2010/0168677 | A1 | 7/2010 | Gabriel et al. |
| 2010/0274198 | A1 | 10/2010 | Bechtold |
| 2011/0054412 | A1 | 3/2011 | Eich et al. |
| 2011/0098658 | A1 | 4/2011 | Enggaard et al. |
| 2012/0283658 | A1* | 11/2012 | Plumptre ................ A61M 5/24 604/211 |

FOREIGN PATENT DOCUMENTS

| | | |
|---|---|---|
| DE | 3645245 C2 | 1/1994 |
| DE | 29703820 | 8/1998 |
| DE | 10232412 A1 | 2/2004 |
| DE | 69629391 T2 | 6/2004 |
| DE | 20317377 U1 | 4/2005 |
| DE | 102005008280 B3 | 7/2006 |
| DE | 102005063311 A1 | 8/2006 |
| DE | 102005044096 A1 | 11/2006 |
| DE | 102005023824 A1 | 12/2006 |
| DE | 102005060929 A1 | 3/2007 |
| DE | 202008011175 U1 | 1/2010 |
| EP | 0762904 A2 | 3/1997 |
| EP | 1304129 | 11/2005 |
| EP | 1819382 A1 | 8/2007 |
| JP | H05337179 A | 12/1993 |
| JP | 2007/509662 A | 4/2007 |
| JP | 2011510775 A | 4/2011 |
| WO | 2000/041754 A1 | 7/2000 |
| WO | 2006040296 A2 | 4/2006 |
| WO | 2008116766 A1 | 10/2008 |
| WO | 2008148864 A1 | 12/2008 |
| WO | 2010056367 A1 | 5/2010 |
| WO | 2010084164 A1 | 7/2010 |
| WO | 2011060785 A1 | 5/2011 |
| WO | 2011/101349 A1 | 8/2011 |
| WO | 2014060369 A1 | 4/2014 |

OTHER PUBLICATIONS

Foundation Warentest, "Insulin pens: the rough sample," Aug. 24, 2006.
Merriam-Webster, Definition of "Button", updated Dec. 5, 2017.

* cited by examiner

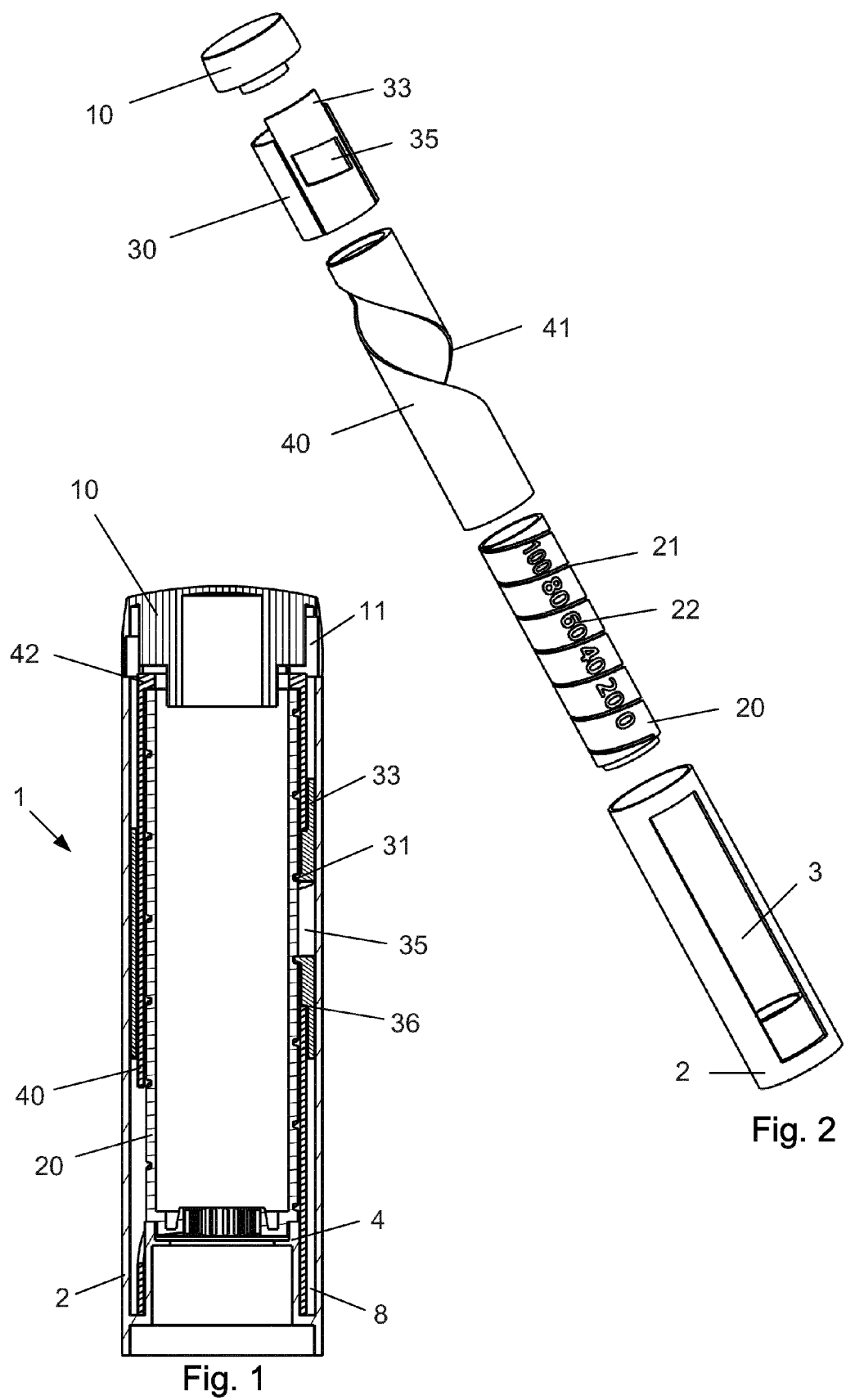

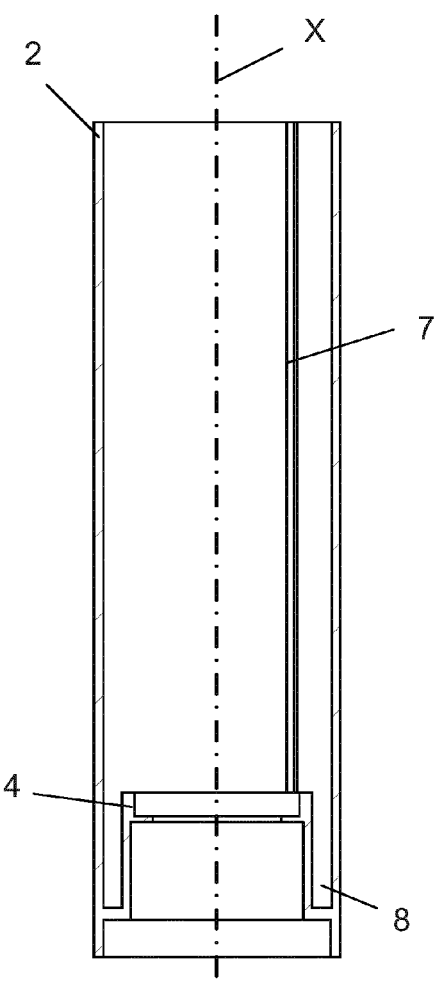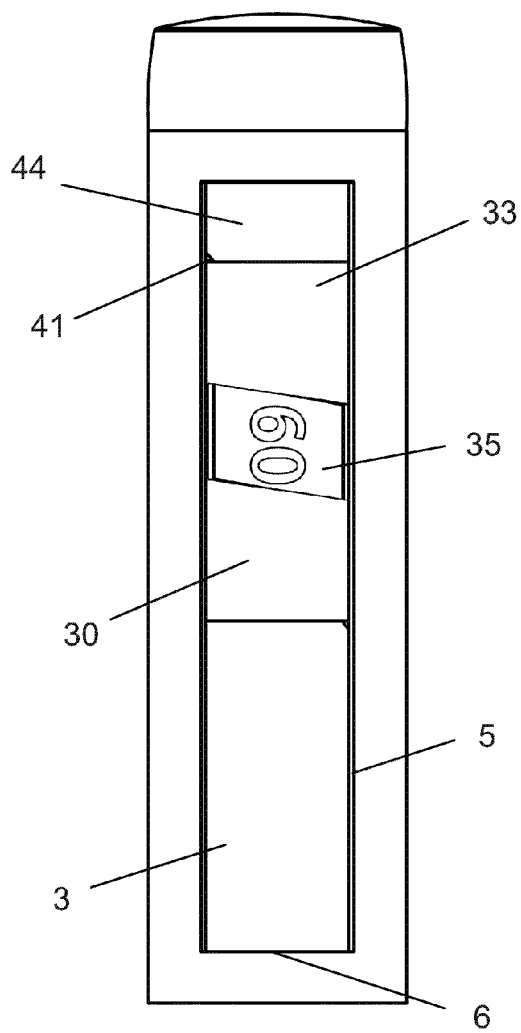

INJECTION DEVICE WITH A SLIDING SCALE

CROSS-REFERENCE TO RELATED APPLICATIONS

This application is a 35 U.S.C. § 371 National Stage application of International Application PCT/EP2013/050806 (published as WO 2013/110538), filed Jan. 17, 2013, which claimed priority of European Patent Application 12152847.5, filed Jan. 27, 2012; this application claims priority under 35 U.S.C. § 119 of U.S. Provisional Application 61/593,956; filed Feb. 2, 2012.

THE TECHNICAL FIELD OF THE INVENTION

The invention relates to an injection device with a large display and especially to a purely mechanical injection device with the ability to display the dose setting size in large ciphers.

DESCRIPTION OF RELATED ART

Many known injection devices and especially pen shaped injection devices have a limited space for the ciphers displaying the dose set by the user.

An injection device having a scale drum which rotate and moves helically out of and away from the housing is disclosed in U.S. Pat. No. 6,004,297. The injection device depictured in FIG. 15-17 is successfully sold by Novo Nordisk NS under the trade name FlexPen®. This injection device requires the user to rotate the scale drum out of the housing when setting a dose, and to manually push back the scale drum into the housing during injection. This limits the possible length of the scale drum as the user needs to reach to the end of the scale drum with his or hers thumb in order to press back the scale drum.

A further injection device having a rotatable scale drum is disclosed in US 2010/0168677. In this injection device the scale drum (66) do not move axially during dose setting but only rotates within the boundaries of the housing. A longitudinal window (54) is provided in the housing through which longitudinal window (54) the indicia printed on the scale drum (66) can be viewed. In order only to view one indicia at the time a sliding window (130) slides axially in the longitudinal window (54). The sliding window (130) is an integral part of the injection sleeve (116) which moves axially out from the housing when a dose is set i.e. the injection device is of the type where a part (the injection sleeve (116)) grow out of the injection device during dose setting and which part is manually pushed back in to the housing during dosing. However, as the sliding window (130) is an integral part of the injection sleeve (116) this defines a limit for the possible axial movement of the sliding window (130) and thus a limit for the size of the indicia printed on the scale drum (66) because the injection sleeve (116) with the sliding window (130) can never be moved further out of the injection device than to allow the user to place his or hers thumb on the injection button (40). In addition the part of the injection sleeve (116) being distal to the sliding window (130) must have a length sufficient to cover the scale drum (66) also when the sliding window (130) is in its most proximal position. This length of the injection sleeve (116) further needs to be concealed by the housing when the sliding window (130) is in its distal position. As a consequence of this a significant part of the scale drum (66) cannot be used for carrying indicia as it is constantly concealed in the non-visible part of the housing.

A different kind of injection device is disclosed in EP 1,1819,382. This injection device has a torsion spring which is tighten during dose setting and wherein the torque of the spring is utilized to perform the injection. This injection device is sold by Novo Nordisk NS under the trade name FlexTouch®. In this particular injection device neither the scale drum nor any other part grow out of the housing during dose setting but the scale drum move helically inside the boundaries of the housing. The rotatable dose setting button is axially retained by the housing and the injection device remains the same length both during dose setting and during injection. This, however, limits the possible length of the scale drum as it must be considerable smaller than the length of the housing in order for it to move helically within the boundaries of the housing.

The known injection devices all have the drawback that the space dedicated for the scale drum and for the indicia indicating the set dose is rather limited. Further there is a desire to design injection devices which allow the user to set even higher doses. This is however quiet difficult as that would require even smaller indicia printed on the scale drum which would create a further obstacle for people with impaired sight.

DESCRIPTION OF THE INVENTION

It is an object of the present invention to provide an injection device in which the size of the individual ciphers indicating the set dose can be increased to enhance visibility. It is further an object to provide a large cipher display mechanism suitable to be implemented in an automatic spring-based and pen-shaped injection device.

The invention is defined in claim 1.

Accordingly, in one aspect of the present invention, an injection device for automatic spring driven injection of a liquid drug, comprises a dose setting mechanism by which a user can set individual dose sizes and a mechanical dose size display for displaying the size of the set dose. The injection device further comprises:

- a housing which defines an interior space and has a longitudinal window,
- a rotatable dose dial button which is axially retained in relation to the housing such that dose dial button is limited to rotational movement and which button is coupled to the dose setting mechanism,
- a rotatable scale drum carrying indicia for indicating the size of the set dose and which scale drum is coupled to the dose dial button such that the scale drum follows rotation of the dose dial button at least during dose setting,
- a sliding element having a window (referred to as a sliding window) and which sliding element is adapted to slide axially in relation to the housing during dose setting, and through which sliding window the indicia carried by the scale drum is visible such that the longitudinal window and the sliding window in combination with the indicia form the dose size display, and wherein
- the movement of the rotatable scale drum is limited to rotation within the interior space defined by the housing during dose setting and wherein the sliding element is coupled to the scale drum such that the sliding element move axially within the boundaries of the housing when the scale drum is rotated.

Since neither the dose dial button nor the scale drum move axially and the scale drum stays within the boundaries of the housing it is possible to utilize the entire surface of the scale drum for carrying the indicia indicating the dose size.

Further, as the sliding element is limited to axial movement within the parameters of the housing and no parts grow out of the housing a larger part of the scale drum can be utilized for carrying indicia as the sliding element can move along the entire scale drum.

The sliding element is preferably threaded to the scale drum and axial guided in the housing such that the sliding element move axial in relation to the housing whenever the scale drum is rotated.

The axial guiding between the sliding element and the housing is preferably constructed as a key and groove connection where the housing carries the key in form of raised bars and the sliding element carries the grooves in form of axial recesses. However, any kind of key and groove would suffice as long as the sliding element slides axially in relation to the housing.

In a further embodiment a sleeve covering the scale drum can be provided. Such sleeve should have a helical opening which in cooperation with the sliding window in the sliding element allows the user to only visible see the relevant indicia of the scale drum.

The axial movement of the sliding element in the helical opening of this sleeve results in a rotation of the sleeve. The pitch of the helical opening of the sleeve is preferably larger than the pitch of the thread of the scale drum such that the scale drum rotates with a higher rotational velocity than the sleeve.

The scale drum is coupled to dose dial button such that they both rotate together. However, in one embodiment this coupling can be made such that they only rotate together when a dose is set where after the dose dial button remains in its position when the scale drum rotate back to its initial position. Such coupling could be any kind of one-way ratchet mechanism which allows the scale drum to rotate in one direction independently of the dose dial button.

The injection device is preferably of the kind in which a torsion spring is strained during dose setting such that a torque is build up in the torsion spring. Such injection device is provided with a user-operable release mechanism which releases the torque of the torsion spring. The torsion spring can be prestrained in which case only a part of the torque is released when activating the release mechanism. The released torque is used to press the set dose out of the cartridge contained in the injection device.

DEFINITIONS

An "injection pen" is typically an injection apparatus having an oblong or elongated shape somewhat like a fountain pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Scale drum" is preferably meant to be a cylinder shaped element carrying indicia indicating the size of the selected dose to the user of the injection pen. "Indicia" is meant to incorporate any kind of printing or otherwise provided symbols e.g. engraved or adhered symbols. These symbols are preferably, but not exclusively, Arabian numbers from "0" to "9".

"Cartridge" is the term used to describe the container containing the drug. Cartridges are usually made from glass but could also be moulded from any suitable polymer. A cartridge or ampoule is preferably sealed at one end by a pierceable membrane which can be pierced e.g. by an injection needle. The opposite end is closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug.

Further the term "injection needle" defines a piercing member adapted to penetrate the skin of a subject for the purpose of delivering or removing a liquid.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which:

FIG. 1 show a cross sectional view of the dose setting mechanism.

FIG. 2 show an exploded view of the dose setting mechanism.

FIG. 3 show a side view of the dose setting mechanism of FIGS. 1 and 2.

FIG. 4 show a view cross sectional view of the housing.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

Figure 5:
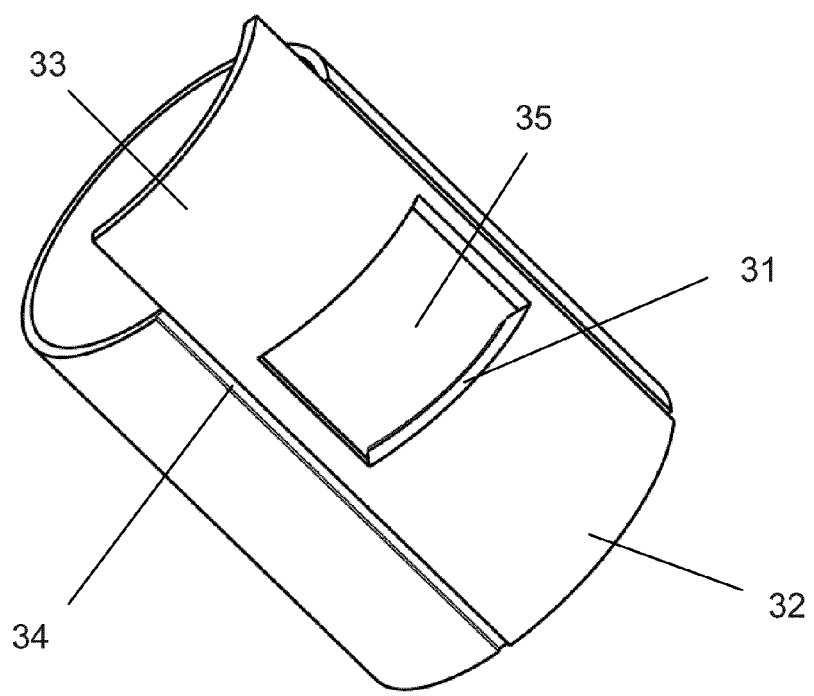
FIG. 5 show a perspective view of the slider.

When in the following terms as "upper" and "lower", "right" and "left", "horizontal" and "vertical", "clockwise"

and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device which usually carries the injection needle whereas the term "proximal end" is meant to refer to the opposite end pointing away from the injection needle and carrying the dose dial button as depictured in FIG. 1.

FIG. 1 and FIG. 2 discloses in different perspectives the end of the injection pen 1 being proximal to the non-shown cartridge containing the drug. At the most proximal end of the housing 2, a dial button 10 is provided which a user can rotate to select a variable dose size. The housing 2 is further provided with a longitudinal window 3 through which longitudinal window 3 the user can visible inspect the scale drum 20. The housing 2 is further provided with an internal projection 4 which supports the scale drum 20.

The scale drum 20 is directly coupled to the dial button 10 to follow rotation of the dial button 10 such that when a user rotates the dial button 10 to select a dose, the scale drum 20 rotates together with the dial button 10. Both the dial button 10 and the scale drum 20 are arranged such that they both rotate without any axial displacement. The connection between the dial button 10 and the scale drum 20 can be made through a releasable coupling such that when the set dose is injected, the dial button 10 does not necessarily rotate back with the scale drum 20.

The longitudinal window 3 is as disclosed in FIG. 3 rectangular and has two longitudinal borders 5 stretching parallel to the centre line X and two radial borders 6 being perpendicular to the centre line X. The window 3 is preferably transparent but could alternatively be an opening in the housing 2. The longitudinal borders 5 can be provided with inwardly raised bars 7 stretching longitudinal along the longitudinal window 3. This can also be seen in FIG. 4 which depictures a cross sectional view of the housing 2. In this embodiment, the raised bars 7 is moulded throughout the entire length of the housing 2 thereby making the raised bars 7 longer than the longitudinal borders 5 of the longitudinal window 3.

The scale drum 20 is on its outer surface provided with a helical track or thread 21. Further, the scale drum carries indicia 22 which can be printed directly on the scale drum or engraved or otherwise provided. In the disclosed embodiment, the indicia from "0" to "100" are helically provided on the scale drum 20, however only every tenth indicia 22 is shown in FIG. 2. In FIG. 3 the indicia "60" is shown in the window 35, however the neighbouring numbers "59" and "61" would normally also appear in the window 35, either fully or partly.

The external helical thread 21 of the scale drum 20 is engaged by a corresponding male thread 31 of a slider 30. The slider 30 disclosed in FIG. 5 is tubular and has a peripheral part 32 of its periphery prolonged by an extension 33 the purpose of which will be explained later. The periphery part 32 is provided between two recesses 34 which engage the two longitudinal bars 7 of the housing 2 such that the slider 30 can only move axially. The periphery part 32 of the slider 30 is further provided with a window 35 through which the user can view the scale drum 20.

Figure 6:
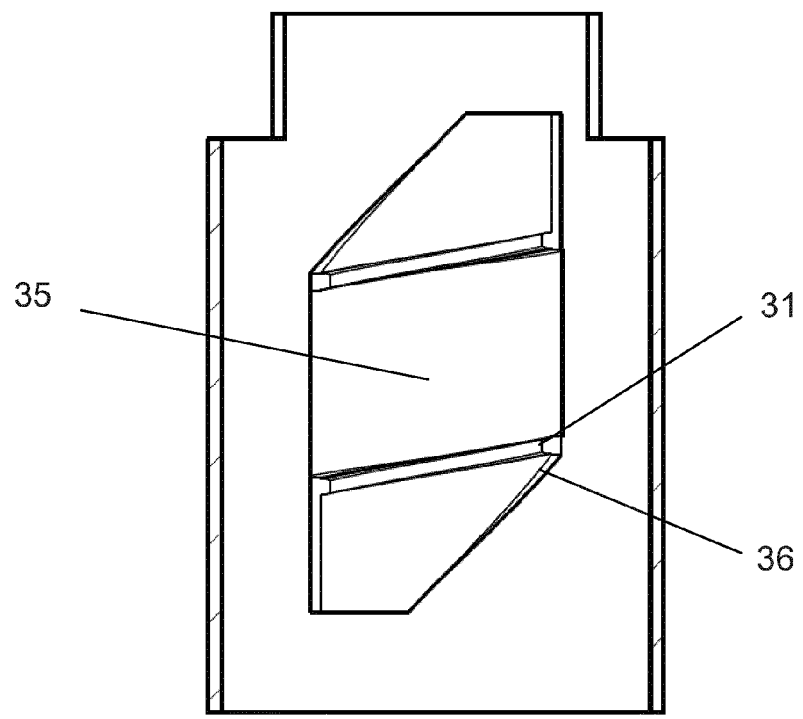
FIG. 6 show a view of the slider as viewed from the inside.
Figures 7, 8:
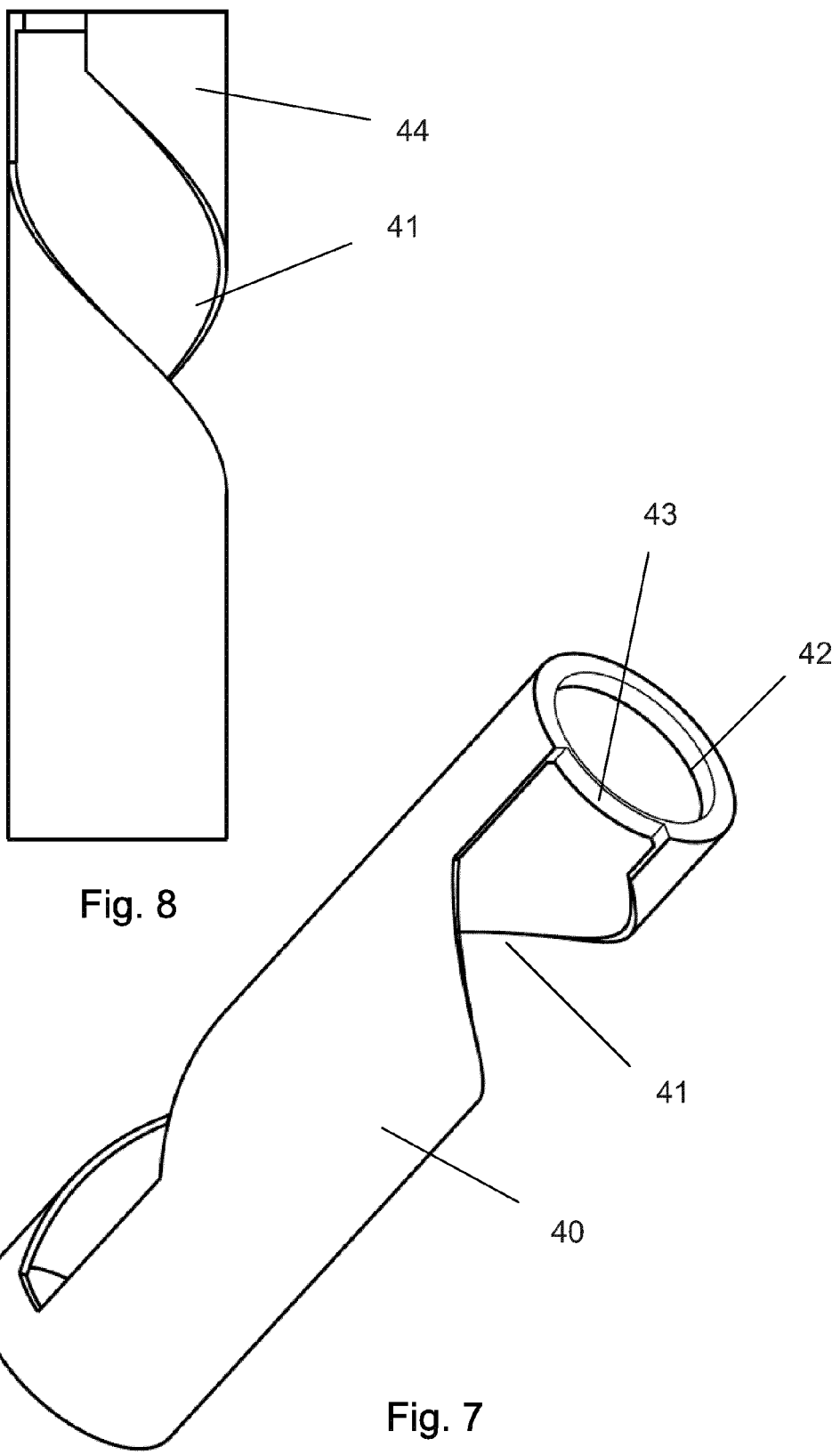
FIG. 7 show a perspective view of the sleeve.
FIG. 8 show a side view of the sleeve.

FIG. 6 depictures the slider 30 viewed from the inside. On two sides of the window 35, the male thread 31 engaging the helical thread 21 of the scale drum 20 is provided. Due to this engagement in combination with the engagement between the recesses 34 and a corresponding longitudinal bars 7 of the housing 2, the slider 30 moves axially whenever the scale drum 20 is rotated. The slider 30 is further provided with a helical guiding surface 36 which interacts with a helical opening 41 in a sleeve 40 depictured in FIGS. 7 and 8. Whenever the slider 30 slides axially it forces the sleeve 40 to rotate due to this engagement between the opening 41 and the guiding surface 36 of the slider 30. The sleeve 40 has at its proximal end a collar 42 which rests on the scale drum 20 however without being connected to the scale drum 20. The sleeve 40 therefore rotates independently of the scale drum 20. Further, at its proximal end the helical opening 41 has an extended access opening 43 making it possible to mount the slider 30 in the helical opening 41 when assembling the mechanism.

In order to set a dose, the user rotates the dial button 10 which in turn rotates the scale drum 20. The rotation of the scale drum 20 in either direction is transferred to an axial movement of the slider 30. The axial movement of the slider 30 and thus the sliding window 35 relatively to the longitudinal window 3 in the housing 2 is coordinated with the helical pattern of the indicia 22 printed on the scale drum 20 such that only one indicia 22 is present in the longitudinal window 3 and the sliding window 35 at the same time.

When the slider 30 moves axially it forces the sleeve 40 to rotate and the peripheral areas 44 of the sleeve 40 surrounding the helical opening 41 will thus cover part of the scale drum 20 and thereby cover the remaining indicia 22 not to be visualized.

The axial length of the slider 30 has to be sufficient long to cover the visible part of the helical track 41 of the sleeve 40 in order to fully prevent the user from viewing the indicia 22 not in sight through the sliding window 35. It can therefore be necessary to provide the periphery part 32 of the slider 30 with an extension 33. This is illustrated in FIG. 3 which discloses a minor part of the track 41 being visible just above the extension 33. In order to fully utilize the length of the scale drum 20, the dose dial button 10 can be provided with a pocket 11 for obtaining this extension 33 when the slider 30 is in its most proximal position. A similar space 7 is provided at the distal end of the housing to obtain the slider 30. The distal part of the slider 30 can off cause also be formed as an extended portion if wanted.

The interior of the scale drum 20 is preferably occupied by a spring driven dosing mechanism as e.g. disclosed in EP 1,819,382. The depictured housing 2 is further connected to a not shown cartridge-holder provided at the distal end of the housing 2. This cartridge-holder supports a not shown cartridge containing the drug. The cartridge-holder can be exchangeable or irreversible connected to the housing 2.

Some preferred embodiments have been shown in the foregoing, but it should be stressed that the invention is not limited to these, but may be embodied in other ways within the subject matter defined in the following claims

The invention claimed is:

1. An injection device for automatic spring driven injection of a liquid drug, comprising:
   a dose setting mechanism by which doses of an individual size can be set by a user,
   the dose setting mechanism further comprises:
   a housing defining an interior space and having a longitudinal window,
   a rotatable dose dial button axially retained and longitudinally fixed in relation to the housing such that the dose dial button is limited to rotational movement, a rotatable scale drum carrying indicia for indicating a size of a set dose wherein the scale drum is functionally coupled to the dose dial button to rotate when the dose dial button is rotated to set the dose, a sliding element provided with a sliding window, wherein the sliding element is adapted to slide axially in relation to the housing during dose setting, and wherein the indicia carried by the scale drum is visible through the sliding window such that the longitudinal window and the sliding window in combination with the indicia form a dose size display for displaying the size of the set dose, and wherein the rotatable scale drum rotates within the interior space defined by the housing during dose setting and the sliding element is coupled to the scale drum such that the sliding element moves axially within boundaries of the housing when the scale drum is rotated.

2. An injection device according to claim 1, wherein the sliding element is provided with an internal thread engaging an external thread provided on the scale drum and wherein the sliding element is further axially guided in the housing to move axially when the scale drum is rotated.

3. An injection device according to claim 2, wherein the axial guiding of the sliding element is controlled by raised bars provided internally in the housing and axial grooves provided on a surface of the sliding element.

4. An injection device according to claim 2, wherein the scale drum is surrounded by a rotatable sleeve having a helical opening.

5. An injection device according to claim 4, wherein the sliding element engages the helical opening of the sleeve.

6. An injection device according to claim 5, wherein the sliding element is provided with guiding surfaces that abut sidewalls of the helical opening of sleeve.

7. An injection device according to claim 1, wherein the dose dial button is releasable coupled to the scale drum.

8. An injection device according to claim 1, wherein a torsion spring is provided that is strained when a user rotates the dose dial button to set the dose such that a torque is built up in the torsion spring and wherein the torque can be released to eject the set dose.

* * * * *